(12) United States Patent
Baba

(10) Patent No.: US 12,372,772 B2
(45) Date of Patent: Jul. 29, 2025

(54) OBJECTIVE OPTICAL SYSTEM FOR ENDOSCOPE AND ENDOSCOPE

(71) Applicant: FUJIFILM Corporation, Tokyo (JP)

(72) Inventor: Tomoyuki Baba, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 508 days.

(21) Appl. No.: 17/811,819

(22) Filed: Jul. 11, 2022

(65) Prior Publication Data

US 2022/0342198 A1    Oct. 27, 2022

Related U.S. Application Data

(63) Continuation of application No. PCT/JP2021/001733, filed on Jan. 19, 2021.

(30) Foreign Application Priority Data

Jan. 20, 2020    (JP) .................................. 2020-007024

(51) Int. Cl.
  *G02B 23/24*    (2006.01)
  *G02B 9/10*    (2006.01)
  (Continued)

(52) U.S. Cl.
  CPC ............. *G02B 23/243* (2013.01); *G02B 9/10* (2013.01); *G02B 13/06* (2013.01); *G02B 13/18* (2013.01)

(58) Field of Classification Search
  CPC ........ G02B 23/243; G02B 9/10; G02B 13/06; G02B 13/18; A61B 1/00
  (Continued)

(56) References Cited

U.S. PATENT DOCUMENTS 5,087,989 A    2/1992    Igarashi
5,175,650 A    12/1992    Takayama et al.
(Continued)

FOREIGN PATENT DOCUMENTS

CN    105278095 A    1/2016
CN    105892037 A    8/2016
(Continued)

OTHER PUBLICATIONS

An Office Action mailed by China National Intellectual Property Administration on Aug. 26, 2023, which corresponds to Chinese Patent Application No. 202180009569.2 and is related to U.S. Appl. No. 17/811,819; with English language translation.
(Continued)

*Primary Examiner* — Thomas K Pham
*Assistant Examiner* — Justin W. Hustoft
(74) *Attorney, Agent, or Firm* — Studebaker Brackett PLLC

(57) ABSTRACT

An objective optical system for an endoscope consisting of, in order from an object side toward an image side: a front group having negative focal power; an aperture stop; and a rear group having positive focal power, wherein: the front group includes only three lenses, which consist of, in order from the object side toward the image side: a first lens having negative focal power; a second lens having negative focal power; and a third lens having positive focal power, the rear group includes only three lenses, which consist of, in order from the object side toward the image side: a fourth lens having positive focal power; a fifth lens having positive focal power; and a sixth lens having negative focal power, the second lens and the third lens are cemented to each other, and the fifth lens and the sixth lens are cemented to each other.

10 Claims, 13 Drawing Sheets

(51) Int. Cl.
*G02B 13/06* (2006.01)
*G02B 13/18* (2006.01)

(58) Field of Classification Search
USPC .......................................................... 359/432
See application file for complete search history.

(56) References Cited

U.S. PATENT DOCUMENTS

| | | | |
|---|---|---|---|
| 5,198,931 | A | 3/1993 | Igarashi |
| 2012/0170142 | A1* | 7/2012 | Hsieh ................. G02B 27/0025 |
| | | | 359/762 |
| 2014/0015999 | A1 | 1/2014 | Miyano |
| 2016/0004064 | A1 | 1/2016 | Harada |
| 2016/0178885 | A1 | 6/2016 | Harada et al. |
| 2016/0238831 | A1 | 8/2016 | Baba |
| 2017/0212329 | A1 | 7/2017 | Hwang et al. |
| 2019/0025568 | A1* | 1/2019 | Matsuura ........... G02B 13/0045 |
| 2019/0187454 | A1 | 6/2019 | Baba |
| 2022/0236553 | A1 | 7/2022 | Baba |

FOREIGN PATENT DOCUMENTS

| | | |
|---|---|---|
| CN | 109932813 A | 6/2019 |
| JP | H02-277015 A | 11/1990 |
| JP | 2596827 B2 | 4/1997 |
| JP | 5635678 B2 | 12/2014 |
| JP | 2016-151629 A | 8/2016 |
| JP | 6266503 B2 | 1/2018 |
| JP | 6313241 B2 | 4/2018 |
| JP | 2019-109356 A | 7/2019 |
| WO | 2021/079684 A1 | 4/2021 |

OTHER PUBLICATIONS

An Office Action; "Notice of Reasons for Refusal," mailed by the Japanese Patent Office on Mar. 14, 2023, which corresponds to Japanese Patent Application No. 2021-572747 and is related to U.S. Appl. No. 17/811,819; with English language translation.

An Office Action mailed by China National Intellectual Property Administration on Mar. 2, 2024, which corresponds to Chinese Patent Application No. 202180009569.2 and is related to U.S. Appl. No. 17/811,819; with English.

International Search Report issued in PCT/JP2021/001733; mailed Mar. 23, 2021.

International Preliminary Report on Patentability (Chapter I) and Written Opinion of the International Searching Authority issued in PCT/JP2021/001733; issued Jul. 26, 2022.

* cited by examiner

OBJECTIVE OPTICAL SYSTEM FOR ENDOSCOPE AND ENDOSCOPE

CROSS REFERENCE TO RELATED APPLICATIONS

The present application is a Continuation of PCT International Application No. PCT/JP2021/001733, filed on Jan. 19, 2021, which claims priority to Japanese Patent Application No. 2020-007024, filed on Jan. 20, 2020. Each application above is hereby expressly incorporated by reference, in its entirety, into the present application.

BACKGROUND

Technical Field

The present disclosure relates to an objective optical system for an endoscope and an endoscope.

Related Art

In the related art, endoscopes have been used for the observation, treatment, and/or the like for the inside of a patient's body in a medical field. JP2596827B, JP5635678B, JP6266503B, JP6313241B, and JP2019-109356A disclose lens systems that can be used as an objective optical system for an endoscope.

In recent years, there has been a demand for an objective optical system for an endoscope which has a larger angle of view and of which various aberrations including a chromatic aberration are more satisfactorily corrected.

SUMMARY

The present disclosure provides an objective optical system for an endoscope which has a larger angle of view and of which various aberrations including a chromatic aberration are more satisfactorily corrected and an endoscope comprising the objective optical system for an endoscope.

An objective optical system for an endoscope according to a first aspect of the present disclosure consists of, in order from an object side toward an image side, a front group having negative focal power, an aperture stop, and a rear group having positive focal power. The front group includes only three lenses, which consist of, in order from the object side toward the image side, a first lens having negative focal power, a second lens having negative focal power, and a third lens having positive focal power, as lenses; the rear group includes only three lenses, which consist of, in order from the object side toward the image side, a fourth lens having positive focal power, a fifth lens having positive focal power, and a sixth lens having negative focal power, as lenses; the second lens and the third lens are cemented to each other; and the fifth lens and the sixth lens are cemented to each other. In a case where a focal length of the front group is denoted by fA and a focal length of the rear group is denoted by fB, Conditional expression (1) is satisfied, which is represented by $$0<|fB/fA|<0.38 \quad (1).$$

In the first aspect of the present disclosure, it is preferable that Conditional expression (1-1) is satisfied, which is represented by $$0<|fB/fA|<0.36 \quad (1\text{-}1).$$

According to a second aspect of the present disclosure, in the aspect, it is preferable that a lens surface of the first lens facing the object side is a flat surface.

According to a third aspect of the present disclosure, in the aspect, in a case where a focal length of the entire system is denoted by f, it is preferable that Conditional expression (2) is satisfied, which is represented by $$0<|f/fA|<0.18 \quad (2),$$

and
it is more preferable that conditional expression (2-1) is satisfied, which is represented by $$0<|f/fA|<0.15 \quad (2\text{-}1).$$

According to a fourth aspect of the present disclosure, in the aspect, in a case where a focal length of the entire system is denoted by f, it is preferable that Conditional expression (3) is satisfied, which is represented by $$0<|f/fB|<0.45 \quad (3),$$

it is more preferable that Conditional expression (3-1) is satisfied, which is represented by $$0.3<|f/fB|<0.45 \quad (3\text{-}1),$$

and
it is still more preferable that Conditional expression (3-2) is satisfied, which is represented by $$0.39<|f/fB|<0.43 \quad (3\text{-}2).$$

According to a fifth aspect of the present disclosure, in the aspect, in a case where a focal length of the first lens is denoted by f1, it is preferable that Conditional expression (4) is satisfied, which is represented by $$0<|f1/fA|<0.2 \quad (4),$$

and
it is more preferable that Conditional expression (4-1) is satisfied, which is represented by $$0<|f1/fA|<0.19 \quad (4\text{-}1).$$

According to a sixth aspect of the present disclosure, in the aspect, in a case where a composite focal length of the second lens and the third lens is denoted by f23, it is preferable that Conditional expression (5) is satisfied, which is represented by $$0<|f23/fA|<0.68 \quad (5),$$

and
it is more preferable that Conditional expression (5-1) is satisfied, which is represented by $$0<|f23/fA|<0.56 \quad (5\text{-}1).$$

An endoscope according to another aspect of the present disclosure comprises the objective optical system for an endoscope according to the aspect of the present disclosure.

"Consisting of" and "consist of" in this specification may intend to include: a lens substantially not having focal power; optical elements other than the lens, such as a stop, a filter, and a cover glass; a lens flange; a lens barrel; and the like in addition to mentioned components.

In this specification, "~group having positive focal power" means that a group has positive focal power as a whole. Likewise, "~group having negative focal power" means that a group has negative focal power as a whole. "Single lens" means one lens that is not cemented. However, a complex aspherical lens (that is, a lens in which a spherical lens and an aspherical film formed on the spherical lens are integrated and which functions as one aspherical lens as a whole) is treated as one lens without being regarded as a cemented lens. The sign of focal power and the shape of the lens surface of a lens including an aspherical surface are considered in a paraxial region unless otherwise specified. "The entire system" means "the objective optical system for an endoscope". "Focal length" used in Conditional expressions is a paraxial focal length. The values of Conditional expressions are values that are obtained in a case where a d line is used as a reference. "d line", "C line", "F line", and "h line" described in this specification are emission lines, and the wavelength of a d line is 587.56 nm (nanometer), the wavelength of a C line is 656.27 nm (nanometer), the wavelength of an F line is 486.13 nm (nanometer), and the wavelength of an h line is 404.66 nm (nanometer).

According to the aspects, the objective optical system for an endoscope of the present disclosure and the endoscope comprising the objective optical system for an endoscope can achieve both an increase in the angle of view and the satisfactory correction of various aberrations including a chromatic aberration.

DETAILED DESCRIPTION

Figure 1:
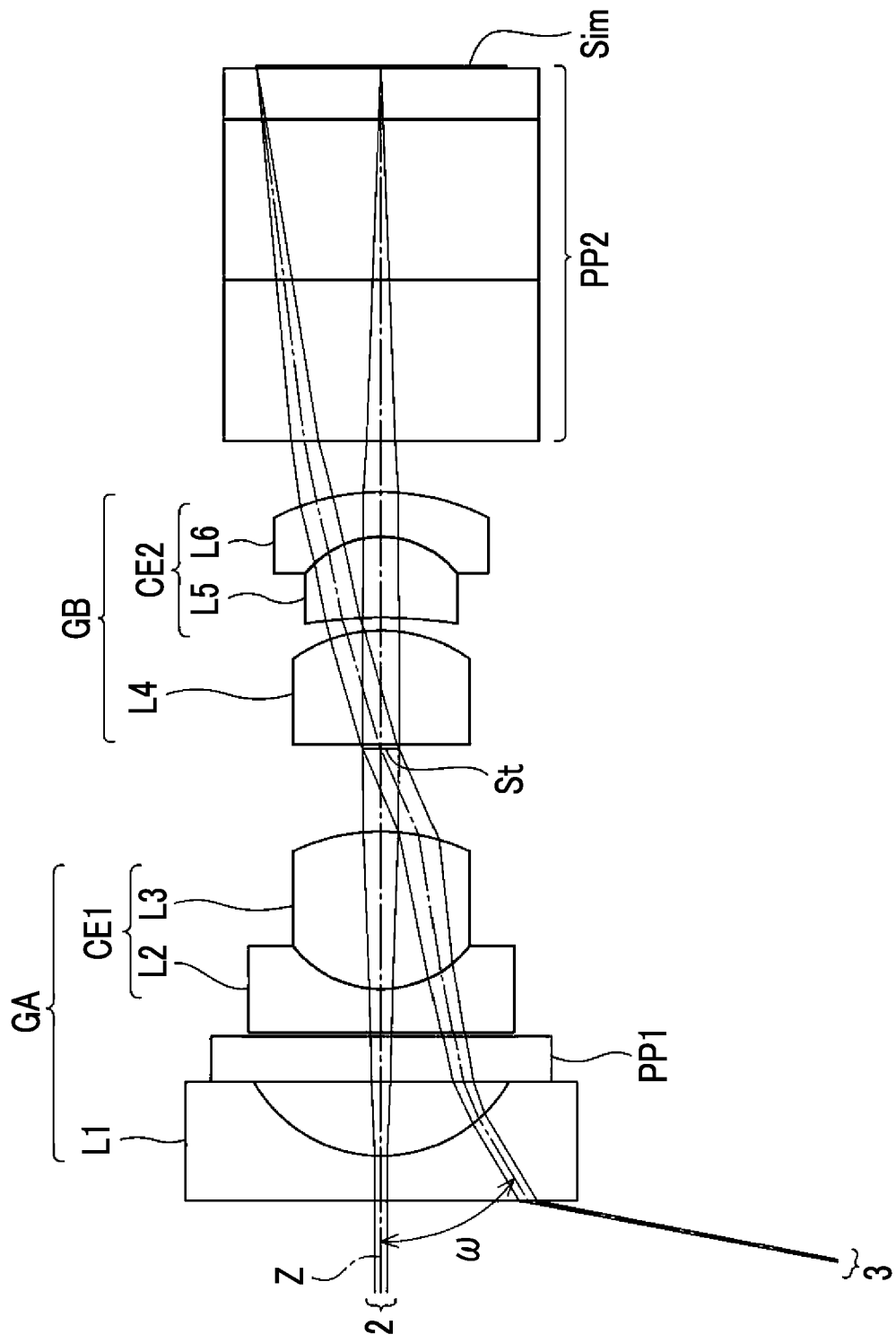
FIG. 1 is a cross-sectional view showing the configuration and optical paths of an objective optical system for an endoscope according to an exemplary embodiment (an objective optical system for an endoscope of Example 1).

Exemplary embodiments of the present disclosure will be described in detail below with reference to the drawings. FIG. 1 is a diagram showing the configuration and optical paths of an objective optical system for an endoscope according to an exemplary embodiment of the present disclosure on a cross section including an optical axis Z, and corresponds to the lens configuration of Example 1 to be described later. In FIG. 1, a left side is an object side, a right side is an image side, the optical paths mean the optical path of on-axis luminous flux 2 and the optical path of luminous flux 3 with the maximum angle of view, and the half angle ω to of view of the principal ray of the luminous flux 3 is also shown. ω shown in FIG. 1 corresponds to the half value of the maximum total angle of view.

The objective optical system for an endoscope according to this exemplary embodiment consists of a front group GA having negative focal power, an aperture stop St, and a rear group GB having positive focal power that are arranged along the optical axis Z in order from the object side toward the image side. Since the negative lens group and the positive lens group are arranged in order from the object side, a retrofocus type lens system is formed. Accordingly, an optical system, which can ensure a back focus and suitably cope with a wide angle of view required for an endoscope, is formed. The aperture stop St shown in FIG. 1 does not necessarily represent a size or a shape and represents the position thereof on the optical axis Z.

The front group GA comprises only three lenses, which consist of, in order from the object side toward the image side, a first lens L1 having negative focal power, a second lens L2 having negative focal power, and a third lens L3 having positive focal power, as lenses. The first lens L1 is a single lens. The second lens L2 and the third lens L3 are cemented to each other and form a first cemented lens CE1. Distortion and field curvature can be suppressed by the first lens L1. Since an axial chromatic aberration and a lateral chromatic aberration can be suppressed by the first cemented lens CE1, it is advantageous in suppressing an axial chromatic aberration and a lateral chromatic aberration over the entire range to a visible range from a short wavelength range near a wavelength of 400 nm (nanometer).

It is preferable that the lens surface of the first lens L1 facing the object side is a flat surface, and the outer diameter of the first lens L1 can be reduced in this case. Further, in a case where the lens surface of the first lens L1 facing the object side is formed of a flat surface, manufacturability can be improved and the adhesion of dust, liquid, and/or the like to the surface of the first lens L1 facing the object side can be reduced.

In the example shown in FIG. 1, an optical member PP1 is disposed between the first lens L1 and the second lens L2. The optical member PP1 is a member of which the incident surface and the emission surface are parallel to each other and which does not have focal power, and is not a lens. The optical member PP1 may be omitted in this exemplary embodiment. The optical member PP1 may be adapted to have a filter function as necessary.

The rear group GB comprises only three lenses, which consist of, in order from the object side toward the image side, a fourth lens L4 having positive focal power, a fifth lens L5 having positive focal power, and a sixth lens L6 having negative focal power, as lenses. The fourth lens L4 is a single lens. The fifth lens L5 and the sixth lens L6 are cemented to each other and form a second cemented lens CE2. A spherical aberration can be suppressed by the fourth lens L4. Since a lateral chromatic aberration can be suppressed by the second cemented lens CE2, it is advantageous in suppressing a lateral chromatic aberration over the entire range to a visible range from a short wavelength range near a wavelength of 400 nm (nanometer).

In the example shown in FIG. 1, an optical member PP2 is disposed between the sixth lens L6 and an image plane Sim. The optical member PP2 is a member of which the incident surface and the emission surface are parallel to each other and which does not have focal power, and is not a lens. A prism, a filter, a cover glass, and/or the like are assumed as the optical member PP2. In a case where a prism for bending an optical path is used as the optical member PP2, optical paths are formed as bent optical paths but a diagram in which optical paths are developed is shown in FIG. 1 for easy understanding. The optical member PP2 may be omitted in this exemplary embodiment.

The objective optical system for an endoscope according to this exemplary embodiment satisfies Conditional expression (1) in a case where the focal length of the front group GA is denoted by fA and the focal length of the rear group GB is denoted by fB. Since it is possible to suitably control balance between the negative focal power of the front group GA and the positive focal power of the rear group GB in a case where |fB/fA| is made to be in the range of Conditional expression (1), it is possible to satisfactorily suppress distortion and field curvature while increasing the angle of view. Further, in a case where the objective optical system for an endoscope according to this exemplary embodiment is adapted to satisfy Conditional expression (1-1), better characteristics can be obtained.

$$0<|fB/fA|<0.38 \tag{1}$$

$$0<|fB/fA|<0.36 \tag{1-1}$$

Furthermore, it is preferable that the objective optical system for an endoscope according to this exemplary embodiment satisfies Conditional expression (2) in a case where the focal length of the entire system is denoted by f. Since it is possible to suitably control balance between the negative focal power of the front group GA and the positive focal power of the rear group GB in a case where |f/fA| is made to be in the range of Conditional expression (2), it is possible to more satisfactorily suppress distortion and field curvature while increasing the angle of view. Moreover, in a case where the objective optical system for an endoscope according to this exemplary embodiment is adapted to satisfy Conditional expression (2-1), better characteristics can be obtained.

$$0<|f/fA|<0.18 \tag{2}$$

$$0<|f/fA|<0.15 \tag{2-1}$$

Further, it is preferable that the objective optical system for an endoscope according to this exemplary embodiment satisfies Conditional expression (3). Since it is possible to suitably control balance between the negative focal power of the front group GA and the positive focal power of the rear group GB in a case where |f/fB| is made to be smaller than the upper limit of Conditional expression (3), it is possible to more satisfactorily field curvature while increasing the angle of view. Furthermore, in a case where the objective optical system for an endoscope according to this exemplary embodiment is adapted to satisfy Conditional expression (3-1), better characteristics can be obtained. In a case where |f/fB| is made to be larger than the lower limit of Conditional expression (3-1), it is advantageous for a reduction in size. Moreover, in a case where the objective optical system for an endoscope according to this exemplary embodiment is adapted to satisfy Conditional expression (3-2), still better characteristics can be obtained.

$$0<|f/fB|<0.45 \tag{3}$$

$$0.3<|f/fB|<0.45 \tag{3-1}$$

$$0.39<|f/fB|<0.43 \tag{3-2}$$

Further, it is preferable that the objective optical system for an endoscope according to this exemplary embodiment satisfies Conditional expression (4) in a case where the focal length of the first lens L1 is denoted by f1. In a case where |f1/fA| is made to be in the range of Conditional expression (4), it is possible to more satisfactorily suppress distortion and field curvature while increasing the angle of view. Furthermore, in a case where the objective optical system for an endoscope according to this exemplary embodiment is adapted to satisfy Conditional expression (4-1), better characteristics can be obtained.

$$0<|f1/fA|<0.2 \tag{4}$$

$$0<|f1/fA|<0.19 \tag{4-1}$$

Further, it is preferable that the objective optical system for an endoscope according to this exemplary embodiment satisfies Conditional expression (5) in a case where the composite focal length of the second lens and the third lens is denoted by f23. In a case where |f23/fA| is made to be in the range of Conditional expression (5), it is possible to more satisfactorily suppress a spherical aberration and field curvature while increasing the angle of view. Furthermore, in a case where the objective optical system for an endoscope according to this exemplary embodiment is adapted to satisfy Conditional expression (5-1), better characteristics can be obtained.

$$0<|f23/fA|<0.68 \tag{5}$$

$$0<|f23/fA|<0.56 \tag{5-1}$$

Since the above-mentioned preferred configurations and possible configurations can be randomly combined, it is preferable that the above-mentioned preferred configurations and possible configurations are appropriately selectively employed according to specifications to be required.

Next, numerical examples of the objective optical system for an endoscope according to the exemplary embodiment of the present disclosure will be described. Basic lens data of Examples 1 to 6 to be described below and diagrams showing aberrations of Examples 1 to 6 are obtained in consideration of the use state of an endoscope in a case where an object (not shown) positioned at a finite distance and having a certain curvature is observed.

Example 1

Since a cross-sectional view showing the configuration and optical paths of an objective optical system for an endoscope of Example 1 is shown in FIG. 1 and a showing method thereof is the same as described above, the repeated description thereof will be omitted here. The basic lens data of the objective optical system for an endoscope of Example 1 are shown in Table 1, and specifications thereof are shown in Table 2. In Table 1, surface numbers, which are obtained in a case where a surface closest to the object side is set as a first surface and a number is increased toward the image side one by one, are shown in the column of Sn, the curvature radii of the respective surfaces are shown in the column of R, and a surface spacing on the optical axis between each surface and a surface adjacent to the image side thereof is shown in the column of D. Further, the refractive indexes of the respective components with respect to a d line are shown in the column of Nd, and the Abbe numbers of the respective components with respect to a d line are shown in the column of νd.

In Table 1, the sign of the curvature radius of a surface having a convex shape toward the object side is set to be positive and the sign of the curvature radius of a surface having a convex shape toward the image side is set to be negative. An object, the aperture stop St, the optical member PP1, and the optical member PP2 are also shown in Table 1 together. In Table 1, OBJ is written in the space of the surface number of a surface corresponding to the object and the surface number and the expression of (St) are written in the space of the surface number of a surface corresponding to the aperture stop St. A value written in the lowest space of the column of D in Table 1 is a spacing between a surface, which is closest to the image side in Table 1, and the image plane Sim.

The value of the focal length f of the entire system and the values of the back focus Bf, the F-Number FNo., and the maximum total angle 2ω of view of the entire system at an air conversion distance are shown in Table 2 with respect to a d line. (°) shown in the space of 2ω means that a unit is a degree.

A degree is used as the unit of an angle and mm (millimeter) is used as the unit of a length in the data of the respective tables, but other appropriate units can also be used since an optical system can be used even in the case of a proportional increase in size or a proportional reduction in size. Further, numerical values, which are rounded off to a predetermined place, are written in each table to be described below.

Figure 2:
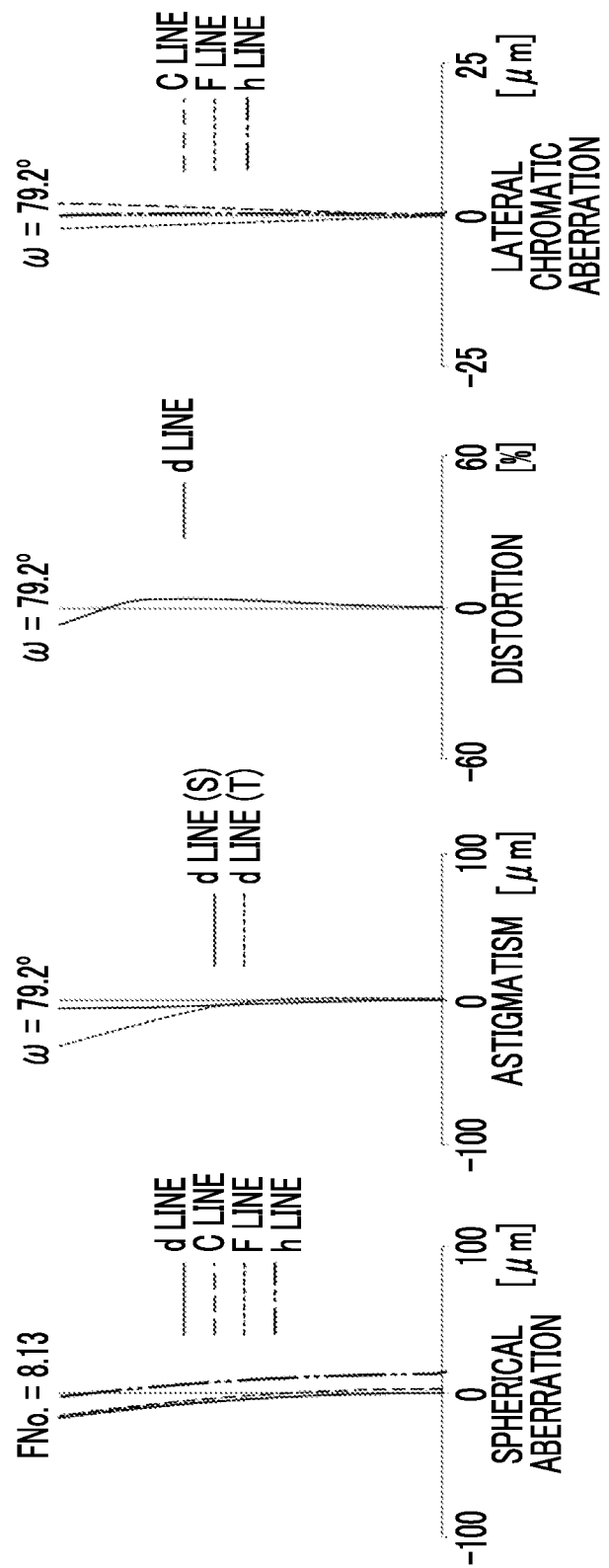
FIG. 2 is a diagram showing the respective aberrations of the objective optical system for an endoscope of Example 1.

A diagram showing the respective aberrations of the objective optical system for an endoscope of Example 1 is shown in FIG. 2. A spherical aberration, astigmatism, distortion, and a lateral chromatic aberration are shown in FIG. 2 in order from the left. In the diagram showing the spherical aberration, aberrations with respect to a d line, a C line, an F line, and an h line are shown by a black solid line, a black long-dashed line, a black short-dashed line, and a black two-dot chain line, respectively. In the diagram showing the astigmatism, an aberration in a sagittal direction with respect to a d line is shown by a solid line and an aberration in a tangential direction with respect to a d line is shown by a short-dashed line. In the diagram showing the distortion, an aberration with respect to a d line is shown by a solid line. In the diagram showing the lateral chromatic aberration, aberrations with respect to a C line, an F line, and an h line are shown by a long-dashed line, a short-dashed line, and a two-dot chain line, respectively. FNo. in the diagram showing the spherical aberration means an F-Number and ω in the diagrams showing the other aberrations means the half angle of view.

Since the symbols, meanings, writing methods, and showing methods for data about Example 1 are the same as those of other examples to be described below unless otherwise specified, the repeated description thereof will be omitted below.

Example 2

Figure 3:
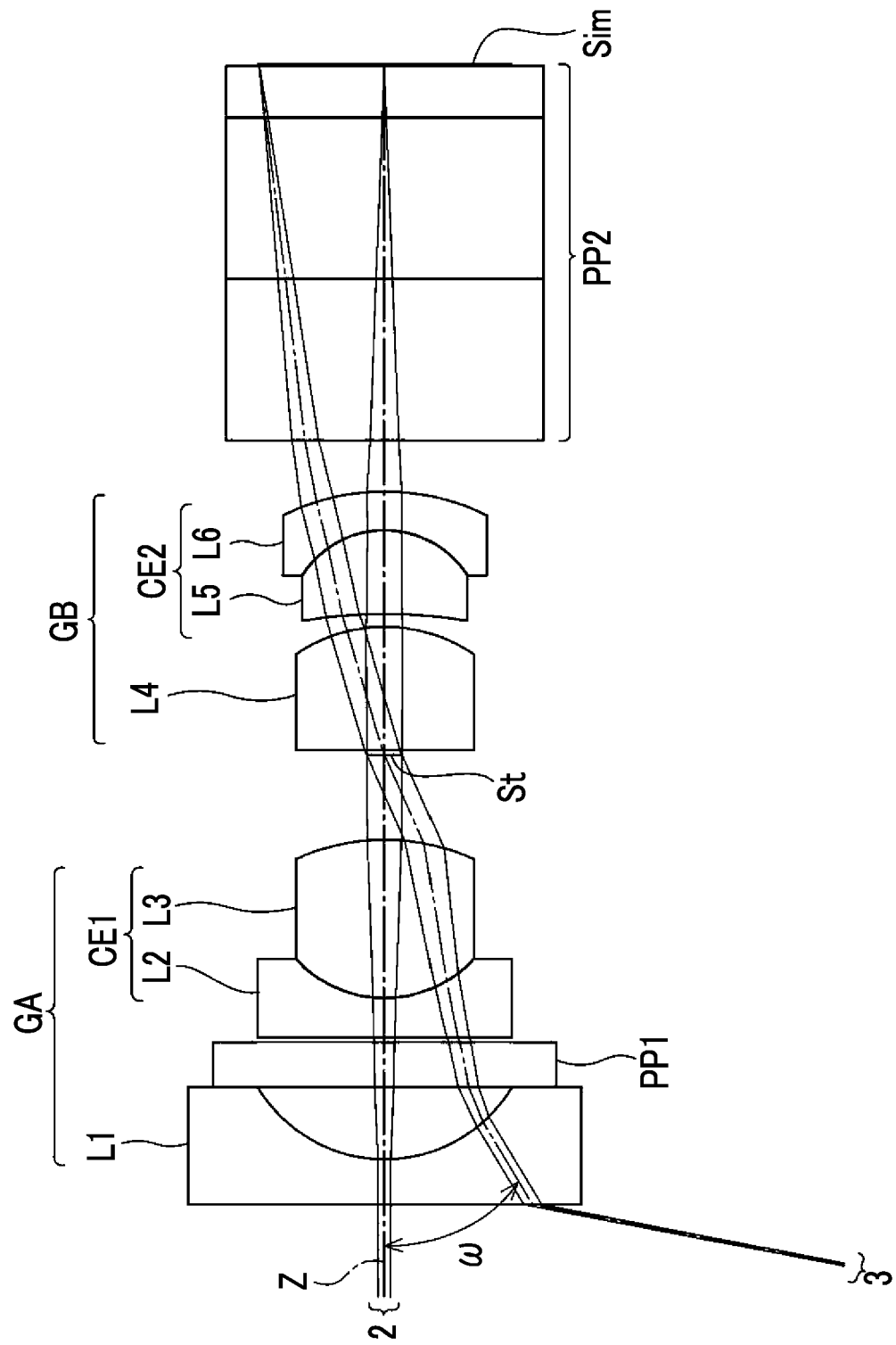
FIG. 3 is a cross-sectional view showing the configuration and optical paths of an objective optical system for an endoscope of Example 2.
Figure 4:
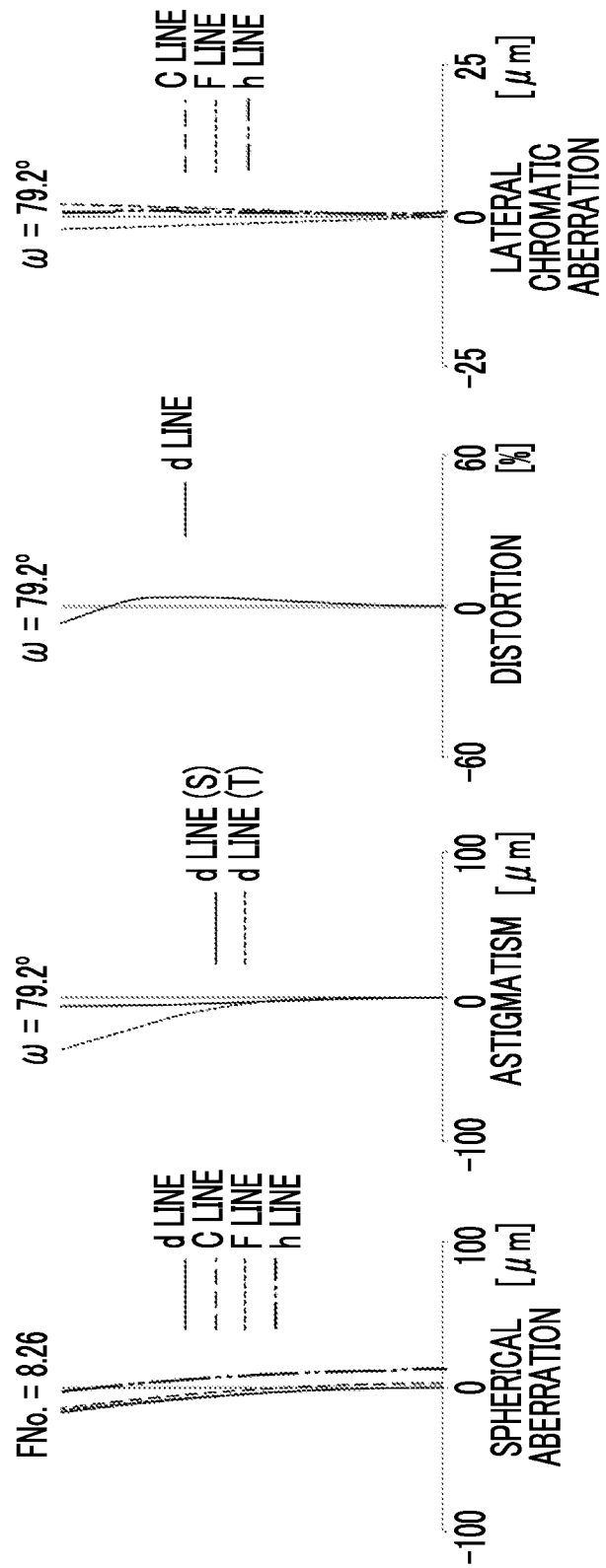
FIG. 4 is a diagram showing the respective aberrations of the objective optical system for an endoscope of Example 2.

A cross-sectional view showing the configuration and optical paths of an objective optical system for an endoscope of Example 2 is shown in FIG. 3, the basic lens data thereof are shown in Table 3, the specifications thereof are shown in Table 4, and a diagram showing the respective aberrations thereof is shown in FIG. 4.

TABLE 1

Example 1

| Sn | R | D | Nd | νd |
|---|---|---|---|---|
| OBJ | 12.0000 | 12.0000 | | |
| 1 | ∞ | 0.3500 | 1.88299 | 40.78 |
| 2 | 1.1757 | 0.5800 | | |
| 3 | ∞ | 0.3500 | 2.00100 | 29.13 |
| 4 | ∞ | 0.0350 | | |
| 5 | ∞ | 0.3300 | 1.91082 | 32.25 |
| 6 | 0.8922 | 1.2300 | 1.69895 | 30.13 |
| 7 | −1.6608 | 0.6450 | | |
| 8(St) | ∞ | 0.0350 | | |
| 9 | ∞ | 0.8900 | 1.43875 | 94.66 |
| 10 | −1.2133 | 0.1000 | | |
| 11 | −3.8959 | 0.6300 | 1.83481 | 42.72 |
| 12 | −0.7768 | 0.3500 | 2.00069 | 25.46 |
| 13 | −1.9004 | 0.4003 | | |
| 14 | ∞ | 1.2500 | 1.55919 | 53.90 |
| 15 | ∞ | 1.2500 | 1.55919 | 53.90 |
| 16 | ∞ | 0.4000 | 1.47144 | 65.41 |
| 17 | ∞ | 0.0181 | | |

TABLE 2

Example 1

| | |
|---|---|
| f | 0.892 |
| Bf | 2.232 |
| FNo. | 8.13 |
| 2ω (°) | 158.4 |

TABLE 3

Example 2

| Sn | R | D | Nd | νd |
|---|---|---|---|---|
| OBJ | 12.0000 | 12.0000 | | |
| 1 | ∞ | 0.3500 | 1.88299 | 40.78 |
| 2 | 1.1750 | 0.5600 | | |
| 3 | ∞ | 0.3500 | 2.00100 | 29.13 |
| 4 | ∞ | 0.0350 | | |
| 5 | ∞ | 0.3000 | 1.91082 | 32.25 |
| 6 | 0.9530 | 1.2300 | 1.69895 | 30.13 |
| 7 | −1.7090 | 0.6600 | | |
| 8(St) | ∞ | 0.0350 | | |
| 9 | ∞ | 0.9600 | 1.43875 | 94.66 |
| 10 | −1.2500 | 0.1000 | | |
| 11 | −3.8410 | 0.6500 | 1.83481 | 42.72 |
| 12 | −0.7780 | 0.3000 | 2.00069 | 25.46 |
| 13 | −1.8180 | 0.3977 | | |
| 14 | ∞ | 1.2500 | 1.55919 | 53.90 |
| 15 | ∞ | 1.2500 | 1.55919 | 53.90 |
| 16 | ∞ | 0.4000 | 1.47144 | 65.41 |
| 17 | ∞ | 0.0170 | | |

TABLE 4

Example 2

| | |
|---|---|
| f | 0.888 |
| Bf | 2.228 |
| FNo. | 8.26 |
| 2ω (°) | 158.4 |

Example 3

Figure 5:
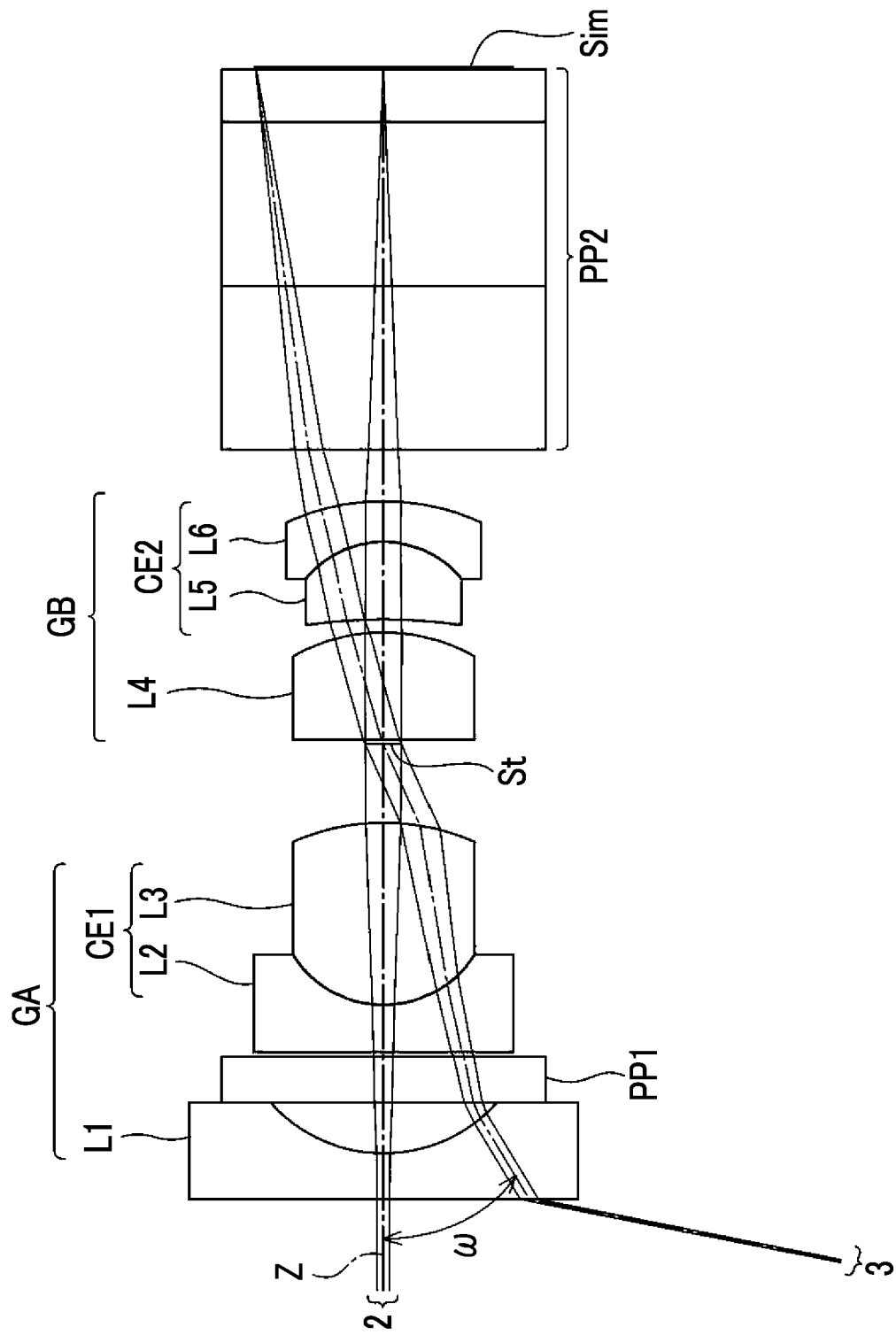
FIG. 5 is a cross-sectional view showing the configuration and optical paths of an objective optical system for an endoscope of Example 3.
Figure 6:
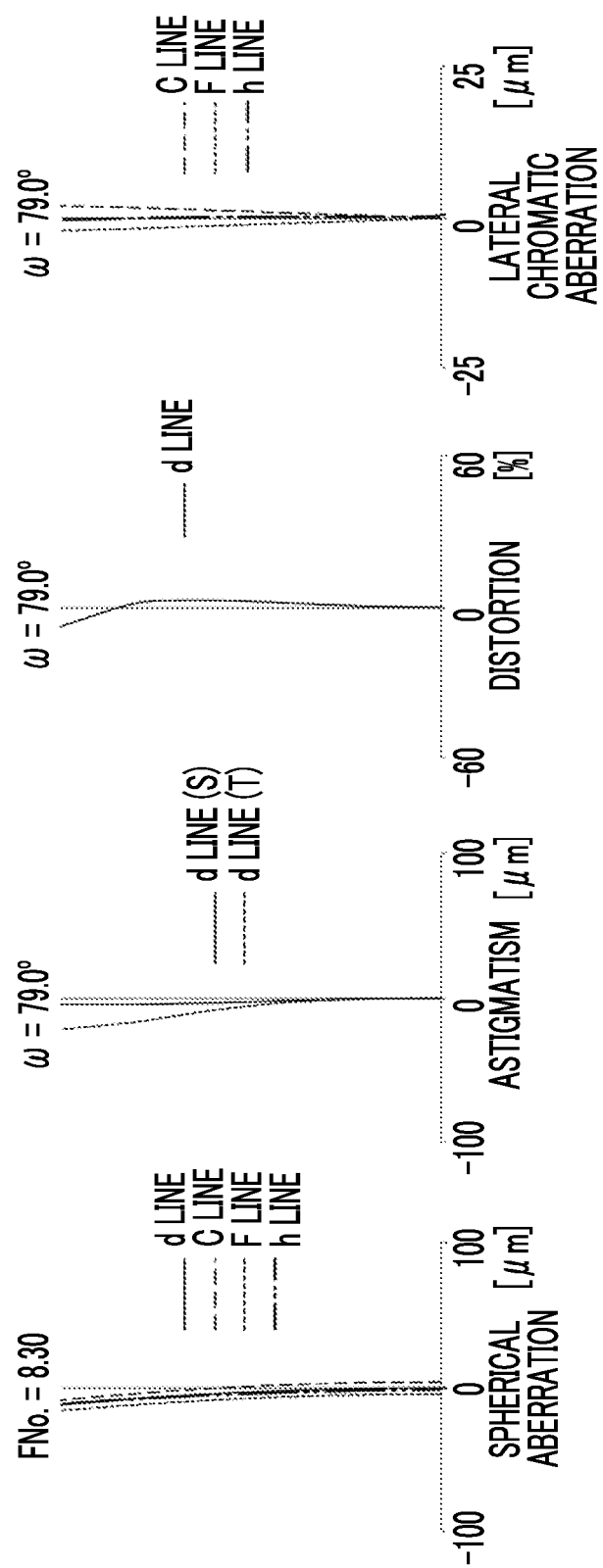
FIG. 6 is a diagram showing the respective aberrations of the objective optical system for an endoscope of Example 3.

A cross-sectional view showing the configuration and optical paths of an objective optical system for an endoscope of Example 3 is shown in FIG. 5, the basic lens data thereof are shown in Table 5, the specifications thereof are shown in Table 6, and a diagram showing the respective aberrations thereof is shown in FIG. 6.

TABLE 5

Example 3

| Sn | R | D | Nd | vd |
|---|---|---|---|---|
| OBJ | 12.0000 | 12.0000 | | |
| 1 | ∞ | 0.3500 | 1.88299 | 40.78 |
| 2 | 1.1750 | 0.3900 | | |
| 3 | ∞ | 0.3500 | 2.00100 | 29.13 |
| 4 | ∞ | 0.0350 | | |
| 5 | ∞ | 0.3000 | 1.91082 | 32.25 |
| 6 | 0.8320 | 1.3900 | 1.71736 | 29.52 |
| 7 | −1.7420 | 0.6000 | | |
| 8(St) | ∞ | 0.0350 | | |
| 9 | ∞ | 0.8100 | 1.49700 | 81.54 |
| 10 | −1.4260 | 0.1000 | | |
| 11 | −3.8410 | 0.5900 | 1.83481 | 42.72 |
| 12 | −0.7780 | 0.3100 | 2.00069 | 25.46 |
| 13 | −1.8180 | 0.3960 | | |
| 14 | ∞ | 1.2500 | 1.55919 | 53.90 |
| 15 | ∞ | 1.2500 | 1.55919 | 53.90 |
| 16 | ∞ | 0.4000 | 1.47144 | 65.41 |
| 17 | ∞ | 0.0211 | | |

TABLE 6

Example 3

| f | 0.899 |
|---|---|
| Bf | 2.229 |
| FNo. | 8.30 |
| 2ω (°) | 158.0 |

Example 4

Figure 7:
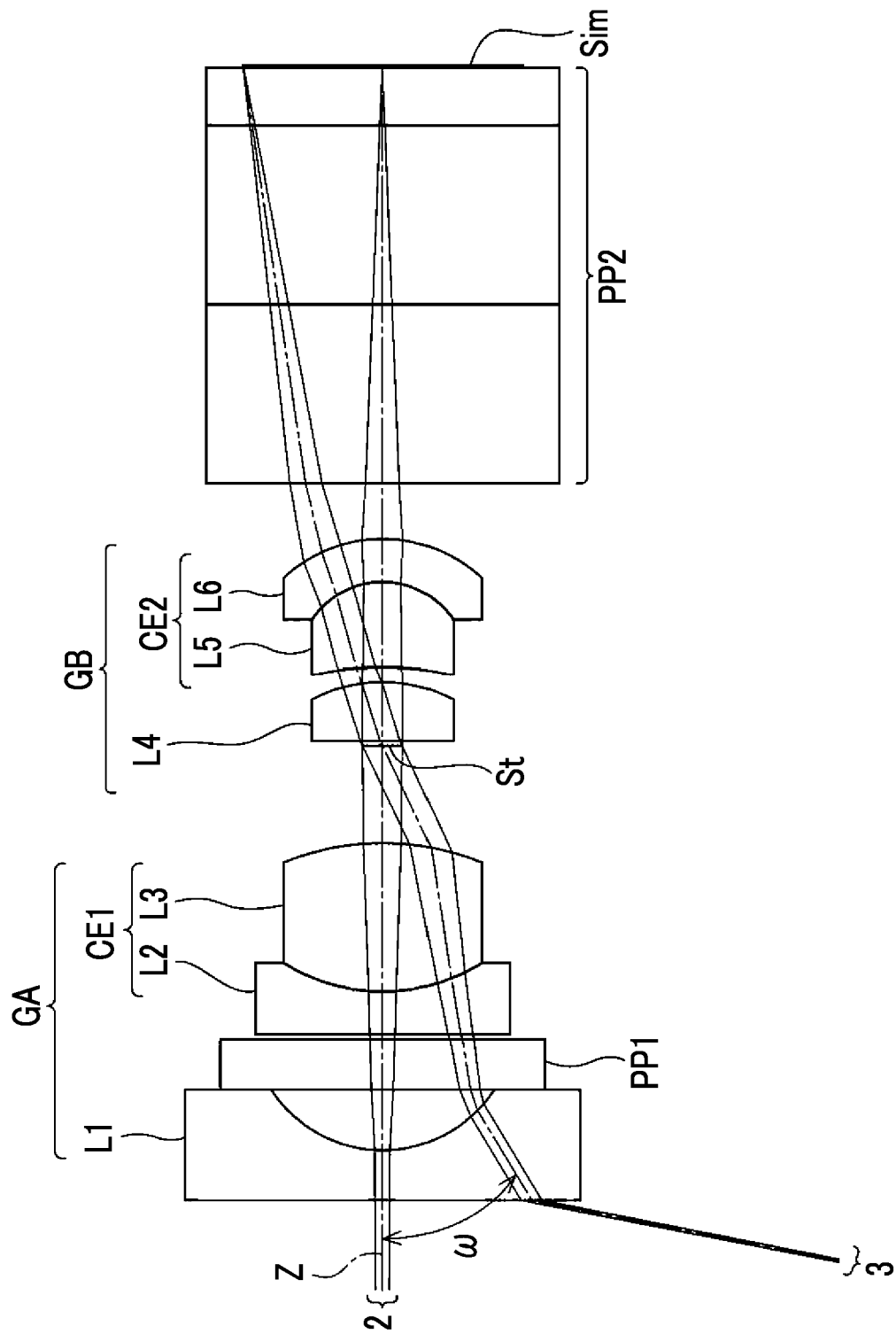
FIG. 7 is a cross-sectional view showing the configuration and optical paths of an objective optical system for an endoscope of Example 4.
Figure 8:
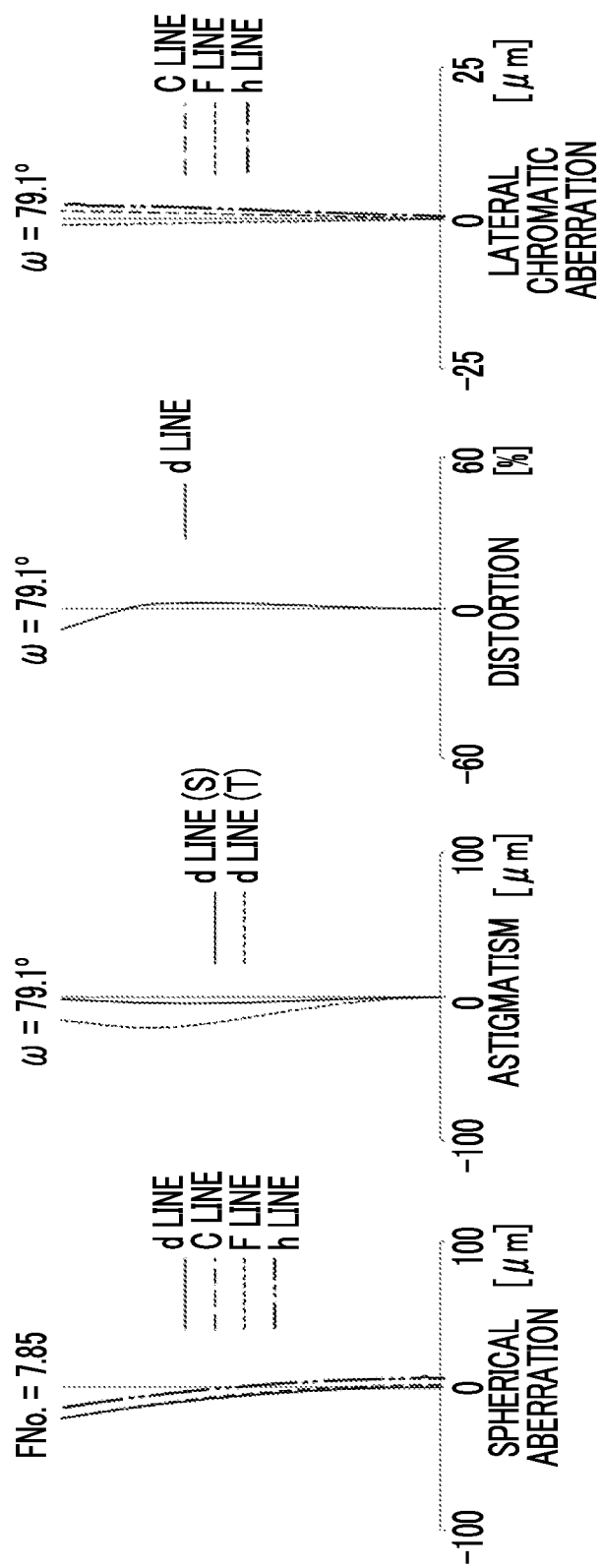
FIG. 8 is a diagram showing the respective aberrations of the objective optical system for an endoscope of Example 4.

A cross-sectional view showing the configuration and optical paths of an objective optical system for an endoscope of Example 4 is shown in FIG. 7, the basic lens data thereof are shown in Table 7, the specifications thereof are shown in Table 8, and a diagram showing the respective aberrations thereof is shown in FIG. 8.

TABLE 7

Example 4

| Sn | R | D | Nd | vd |
|---|---|---|---|---|
| OBJ | 10.1690 | 10.1690 | | |
| 1 | ∞ | 0.3500 | 1.88299 | 40.78 |
| 2 | 0.9452 | 0.4252 | | |
| 3 | ∞ | 0.3500 | 2.00069 | 25.46 |
| 4 | ∞ | 0.0350 | | |
| 5 | ∞ | 0.3000 | 1.91082 | 32.25 |
| 6 | 1.3346 | 1.0346 | 1.78880 | 28.43 |
| 7 | −1.8875 | 0.6791 | | |
| 8(St) | ∞ | 0.0350 | | |
| 9 | ∞ | 0.4101 | 1.43875 | 94.66 |
| 10 | −1.0873 | 0.1000 | | |
| 11 | −2.2322 | 0.5922 | 1.59522 | 67.73 |
| 12 | −0.6061 | 0.3000 | 2.00069 | 25.46 |
| 13 | −1.0366 | 0.3893 | | |
| 14 | ∞ | 1.2500 | 1.55919 | 53.90 |

TABLE 7-continued

Example 4

| Sn | R | D | Nd | vd |
|---|---|---|---|---|
| 15 | ∞ | 1.2500 | 1.55919 | 53.90 |
| 16 | ∞ | 0.4000 | 1.47144 | 65.41 |
| 17 | ∞ | 0.0161 | | |

TABLE 8

Example 4

| f | 0.891 |
|---|---|
| Bf | 2.208 |
| FNo. | 7.85 |
| 2ω (°) | 158.2 |

Example 5

Figure 9:
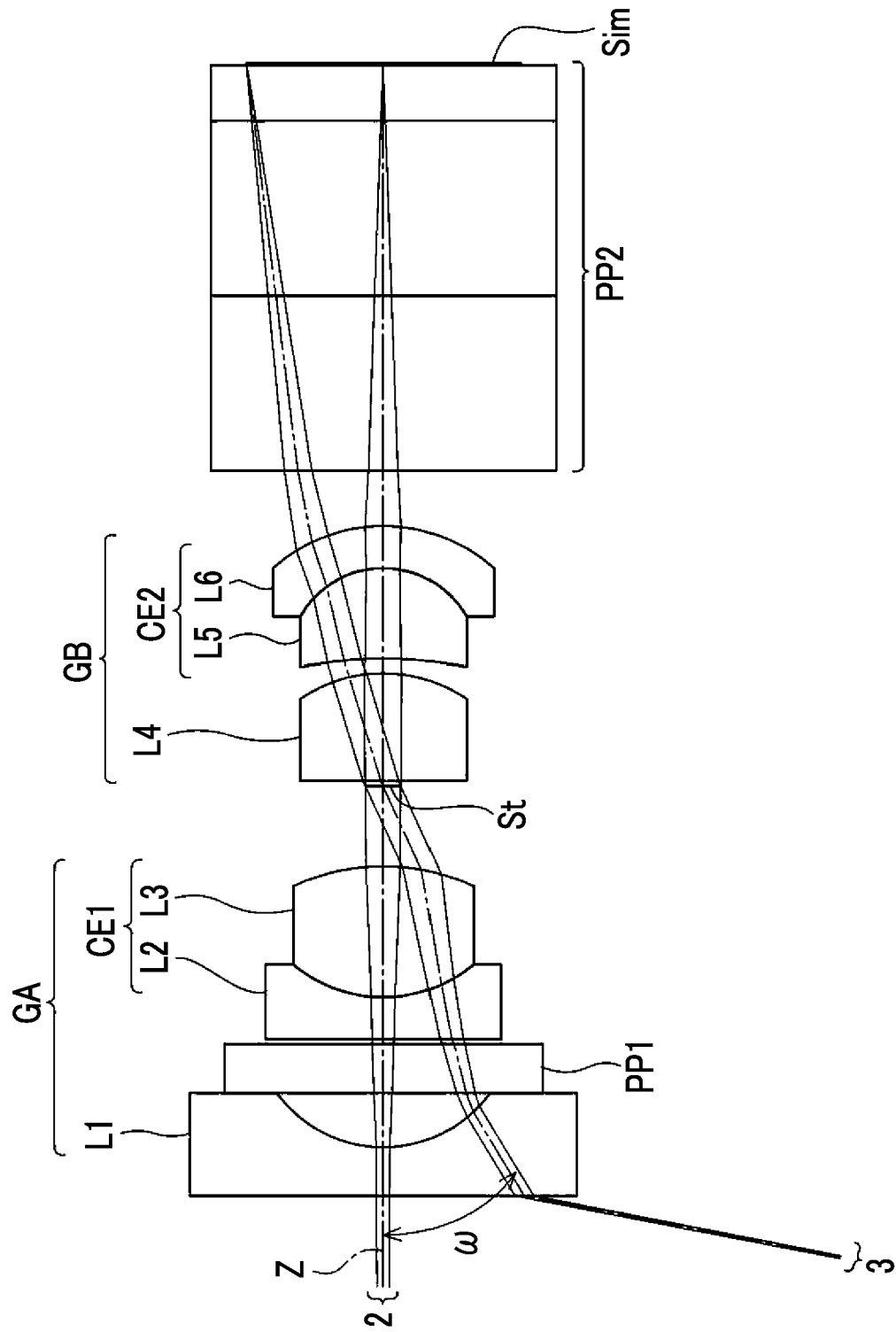
FIG. 9 is a cross-sectional view showing the configuration and optical paths of an objective optical system for an endoscope of Example 5.
Figure 10:
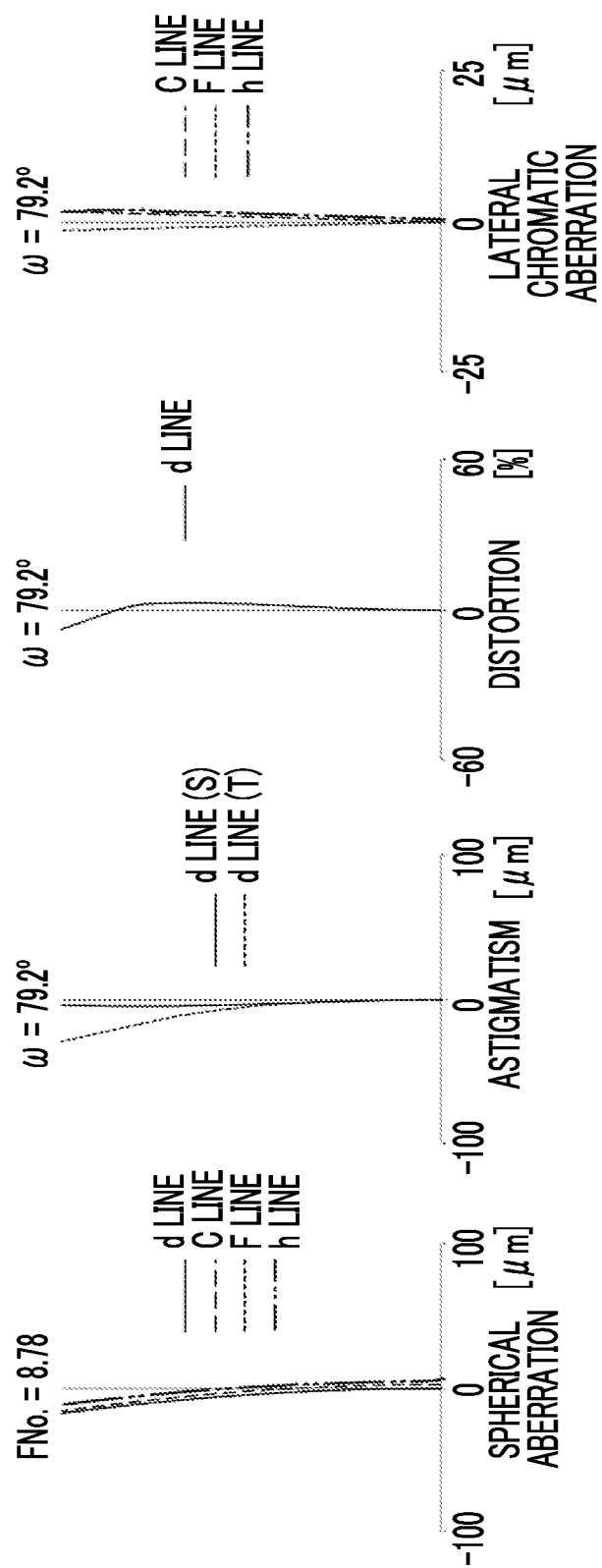
FIG. 10 is a diagram showing the respective aberrations of the objective optical system for an endoscope of Example 5.

A cross-sectional view showing the configuration and optical paths of an objective optical system for an endoscope of Example 5 is shown in FIG. 9, the basic lens data thereof are shown in Table 9, the specifications thereof are shown in Table 10, and a diagram showing the respective aberrations thereof is shown in FIG. 10.

TABLE 9

Example 5

| Sn | R | D | Nd | vd |
|---|---|---|---|---|
| OBJ | 11.1920 | 11.1920 | | |
| 1 | ∞ | 0.3500 | 1.88299 | 40.78 |
| 2 | 0.9622 | 0.3873 | | |
| 3 | ∞ | 0.3500 | 1.48749 | 70.24 |
| 4 | ∞ | 0.0350 | | |
| 5 | ∞ | 0.3000 | 1.88299 | 40.78 |
| 6 | 1.0228 | 0.9356 | 1.68893 | 31.07 |
| 7 | −1.5544 | 0.5732 | | |
| 8(St) | ∞ | 0.0350 | | |
| 9 | ∞ | 0.7723 | 1.43875 | 94.66 |
| 10 | −1.0783 | 0.1000 | | |
| 11 | −3.2415 | 0.6470 | 1.59522 | 67.73 |
| 12 | −0.6935 | 0.3000 | 2.00069 | 25.46 |
| 13 | −1.2093 | 0.3974 | | |
| 14 | ∞ | 1.2500 | 1.55919 | 53.90 |
| 15 | ∞ | 1.2500 | 1.55919 | 53.90 |
| 16 | ∞ | 0.4000 | 1.47144 | 65.41 |
| 17 | ∞ | 0.0142 | | |

TABLE 10

Example 5

| f | 0.886 |
|---|---|
| Bf | 2.221 |
| FNo. | 8.78 |
| 2ω (°) | 158.4 |

Example 6

Figure 11:
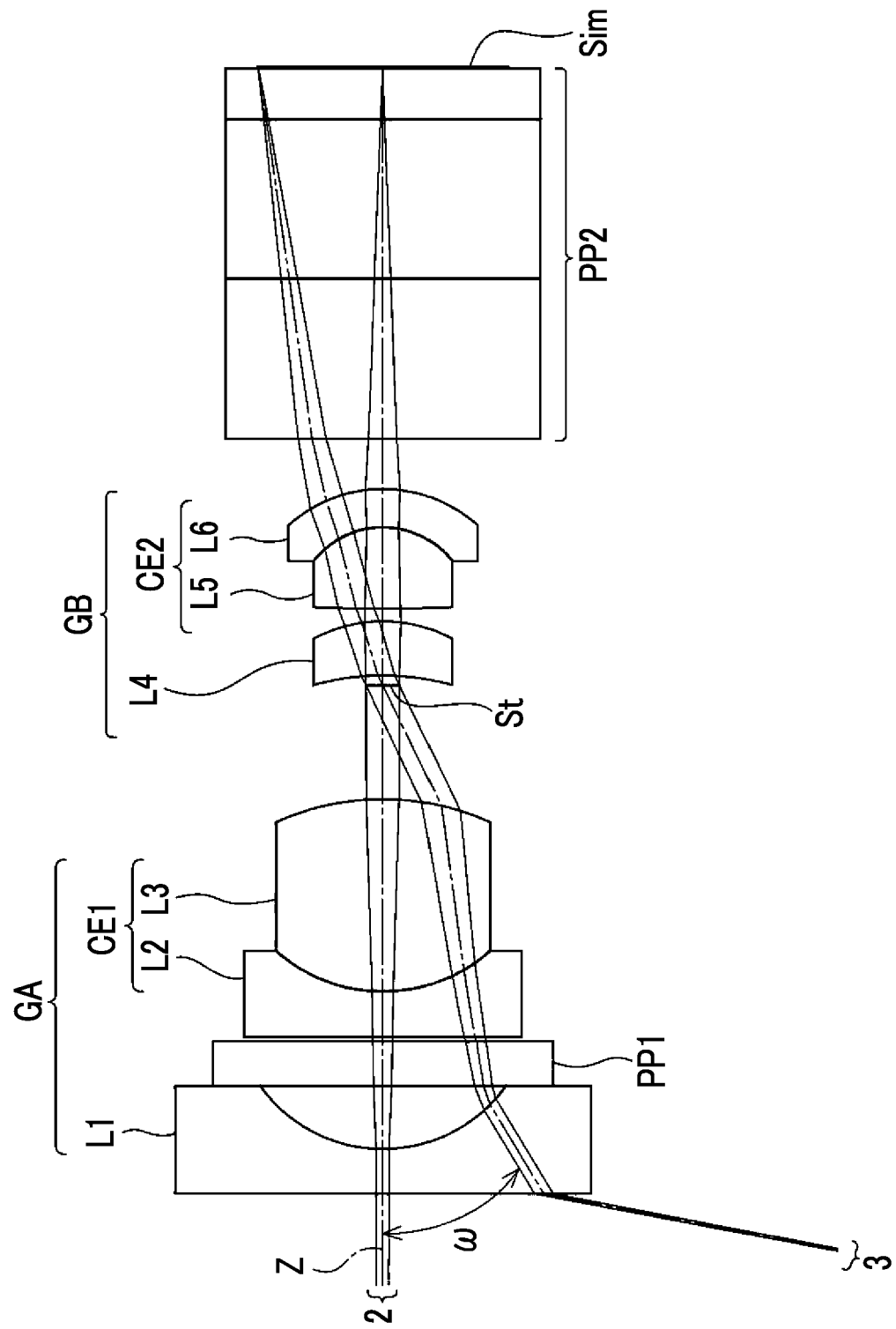
FIG. 11 is a cross-sectional view showing the configuration and optical paths of an objective optical system for an endoscope of Example 6.
Figure 12:
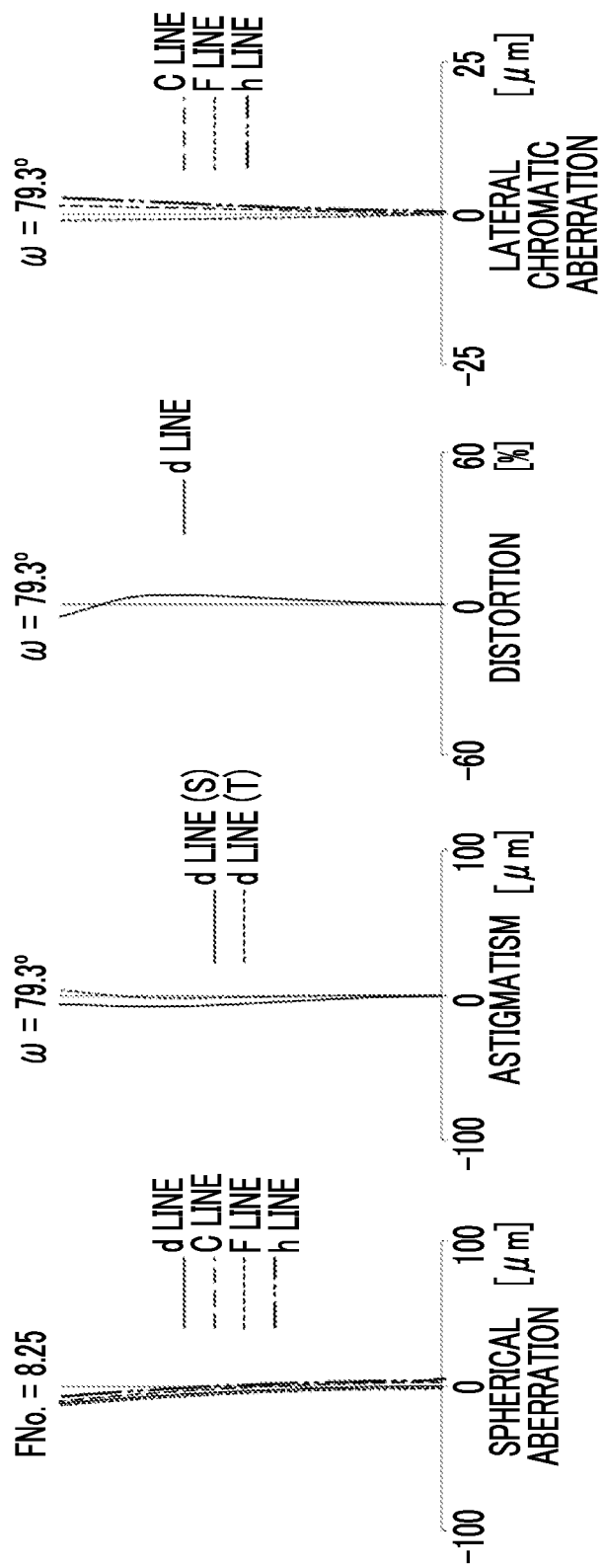
FIG. 12 is a diagram showing the respective aberrations of the objective optical system for an endoscope of Example 6.

A cross-sectional view showing the configuration and optical paths of an objective optical system for an endoscope of Example 6 is shown in FIG. 11, the basic lens data thereof are shown in Table 11, the specifications thereof are shown in Table 12, and a diagram showing the respective aberrations thereof is shown in FIG. 12.

TABLE 11

Example 6

| Sn | R | D | Nd | vd |
|---|---|---|---|---|
| OBJ | 12.0000 | 12.0000 | | |
| 1 | ∞ | 0.3500 | 1.88299 | 40.78 |
| 2 | 1.2089 | 0.4943 | | |
| 3 | ∞ | 0.3500 | 2.00069 | 25.46 |
| 4 | ∞ | 0.0350 | | |
| 5 | ∞ | 0.3497 | 1.95375 | 32.32 |
| 6 | 1.2884 | 1.5093 | 1.78880 | 28.43 |
| 7 | −2.1035 | 0.8958 | | |
| 8(St) | ∞ | 0.0765 | | |
| 9 | −2.0580 | 0.4244 | 1.49700 | 81.54 |
| 10 | −1.1806 | 0.1000 | | |
| 11 | 13.3819 | 0.6375 | 1.49700 | 81.54 |
| 12 | −0.7050 | 0.3000 | 2.00069 | 25.46 |
| 13 | −1.1319 | 0.3959 | | |
| 14 | ∞ | 1.2500 | 1.55919 | 53.90 |
| 15 | ∞ | 1.2500 | 1.55919 | 53.90 |
| 16 | ∞ | 0.4000 | 1.47144 | 65.41 |
| 17 | ∞ | 0.0111 | | |

TABLE 12

Example 6

| f | 0.887 |
|---|---|
| Bf | 2.221 |
| FNo. | 8.25 |
| 2ω (°) | 158.6 |

Values of Conditional expressions (1) to (5) corresponding to the objective optical systems for an endoscope of Examples 1 to 6 are shown in Table 13. In Examples 1 to 6, a d line is used as a reference wavelength. Table 13 shows values with respect to a d line.

TABLE 13

| Expression number | Conditional expression | Example 1 | Example 2 | Example 3 | Example 4 | Example 5 | Example 6 |
|---|---|---|---|---|---|---|---|
| (1) | \|fB/fA\| | 0.184 | 0.221 | 0.203 | 0.211 | 0.352 | 0.057 |
| (2) | \|f/fA\| | 0.073 | 0.089 | 0.083 | 0.091 | 0.148 | 0.023 |
| (3) | \|f/fB\| | 0.396 | 0.403 | 0.408 | 0.429 | 0.421 | 0.411 |
| (4) | \|f1/fA\| | 0.109 | 0.134 | 0.123 | 0.109 | 0.182 | 0.036 |
| (5) | \|f23/fA\| | 0.319 | 0.398 | 0.359 | 0.292 | 0.558 | 0.092 |

It is found from the above-mentioned data that each of the objective optical systems for an endoscope of Examples 1 to 6 satisfies Conditional expressions (1) to (5) and is adapted to have a wide angle of view of 155° or more and various aberrations including a chromatic aberration over the entire range to a visible range from a short wavelength range near a wavelength of 400 nm (nanometer) are satisfactorily corrected.

Figure 13:
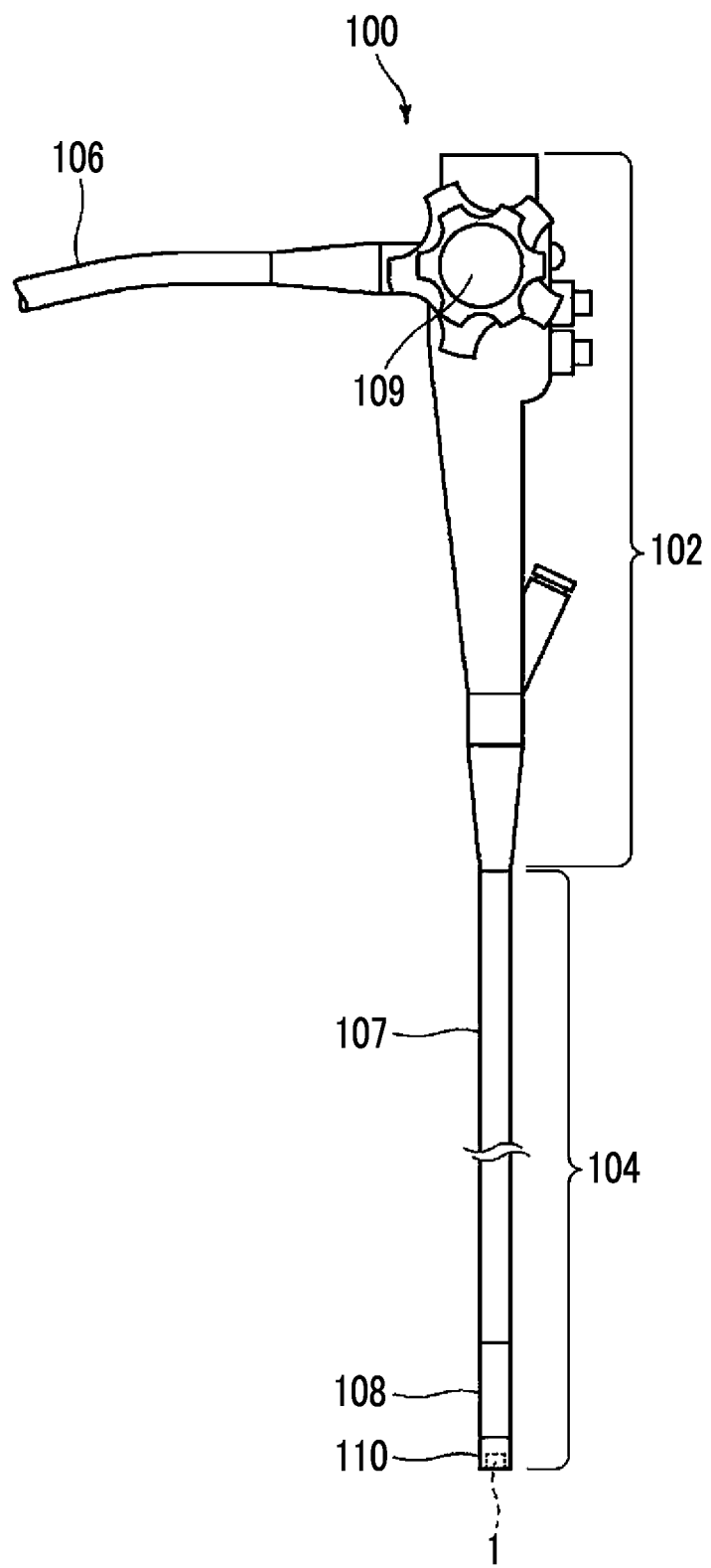
FIG. 13 is a diagram showing the schematic configuration of an endoscope according to an exemplary embodiment.

Next, an endoscope according to an exemplary embodiment of the present disclosure will be described. A diagram showing the entire schematic configuration of the endoscope according to the exemplary embodiment of the present disclosure is shown in FIG. 13. The endoscope 100 shown in FIG. 13 mainly comprises an operation part 102, an insertion part 104, and a universal cord 106 that is to be connected to a connector part (not shown). A large portion of the insertion part 104 is a soft portion 107 that is bendable in any direction along an insertion path, a bendable portion 108 is connected to the distal end of the soft portion 107, and a distal end portion 110 is connected to the distal end of the bendable portion 108. The bendable portion 108 is provided to allow the distal end portion 110 to face in a desired direction, and can be operated to be bent by the rotational movement of bending operation knobs 109 provided on the operation part 102. An objective optical system 1 for an endoscope according to the exemplary embodiment of the present disclosure is provided in the distal end of the distal end portion 110. The objective optical system 1 for an endoscope is schematically shown in FIG. 13.

Since the endoscope according to this exemplary embodiment comprises the objective optical system for an endoscope according to the exemplary embodiment of the present disclosure, an observation can be made with a wide angle of view. Further, since the endoscope can acquire a good image over the entire range to a visible range from a short wavelength range near a wavelength of 400 nm (nanometer), the endoscope can be suitably applied to the observation of an image in which blood vessels, surface structures, and the like are enhanced and which is obtained from the combination of the use of white light and a laser beam having a wavelength of about 400 nm (nanometer) and image processing.

The present disclosure has been described above using the exemplary embodiments and Examples, but the present disclosure can have various modifications without being limited to the exemplary embodiments and Examples. For example, the curvature radius, the surface spacing, the refractive index, and the Abbe number of each lens may have other values without being limited to the values shown in the respective numerical examples.

The entire content of the present disclosure of Japanese Patent Application No. 2020-007024, filed Jan. 20, 2020, is incorporated in this specification by reference. All documents, patent applications, and technical standards disclosed in this specification are incorporated in this specification by reference so that the incorporation of each of the documents, the patent applications, and the technical standards by reference is specific and is as detailed as that in a case where the documents, the patent applications, and the technical standards are described individually.

What is claimed is:

1. An objective optical system for an endoscope consisting of, in order from an object side toward an image side:
   a front group having negative focal power;
   an aperture stop; and
   a rear group having positive focal power, wherein:
   the front group includes only three lenses, which consist of, in order from the object side toward the image side:
      a first lens having negative focal power; a second lens having negative focal power; and a third lens having positive focal power, as lenses,
   the rear group includes only three lenses, which consist of, in order from the object side toward the image side:
      a fourth lens having positive focal power; a fifth lens having positive focal power; and a sixth lens having negative focal power, as lenses, the second lens and the third lens are cemented to each other, the fifth lens and the sixth lens are cemented to each other, in a case where
a focal length of the front group is denoted by fA and a focal length of the rear group is denoted by fB, Conditional expression (1) is satisfied, which is represented by $$0<|fB/fA|<0.38 \quad (1),$$

and in a case where a focal length of the objective optical system for an endoscope is denoted by f, Conditional expression (3-2) is satisfied, which is represented by $$0.39<|f/fB|<0.43 \quad (3\text{-}2).$$

2. The objective optical system for an endoscope according to claim 1, wherein a lens surface of the first lens facing the object side is a flat surface.

3. The objective optical system for an endoscope according to claim 1, wherein:

Conditional expression (2) is satisfied, which is represented by $$0<|f/fA|<0.18 \quad (2).$$

4. The objective optical system for an endoscope according to claim 1 wherein: in a case where a focal length of the first lens is denoted by f1, Conditional expression (4) is satisfied, which is represented by $$0<|f1/fA|<0.2 \quad (4).$$

5. The objective optical system for an endoscope according to claim 1, wherein:

in a case where a composite focal length of the second lens and the third lens is denoted by f23, Conditional expression (5) is satisfied, which is represented by $$0<|f23/fA|<0.68 \quad (5).$$

6. The objective optical system for an endoscope according to claim 1, wherein Conditional expression (1-1) is satisfied, which is represented by $$0<|fB/fA|<0.36 \quad (1\text{-}1).$$

7. The objective optical system for an endoscope according to claim 3, wherein Conditional expression (2-1) is satisfied, which is represented by $$0<|f/fA|<0.15 \quad (2\text{-}1).$$

8. The objective optical system for an endoscope according to claim 4, wherein Conditional expression (4-1) is satisfied, which is represented by $$0<|f1/fA|<0.19 \quad (4\text{-}1).$$

9. The objective optical system for an endoscope according to claim 5, wherein Conditional expression (5-1) is satisfied, which is represented by $$0<|f23/fA|<0.56 \quad (5\text{-}1).$$

10. An endoscope comprising:
the objective optical system for an endoscope according to claim 1.

* * * * *